United States Patent
Reddy et al.

(10) Patent No.: US 8,703,788 B2
(45) Date of Patent: Apr. 22, 2014

(54) POLYMORPH OF NILOTINIB HYDROCHLORIDE

(76) Inventors: Bandi Parthasaradhi Reddy, Hyderabad (IN); Kura Rathnakar Reddy, Hyderabad (IN); Dasari Muralidhara Reddy, Hyderabad (IN); Thungathurthy Srinivasa Rao, Hyderabad (IN); Bandi Vamsi Krishna, Hyderabad (IN)

( * ) Notice: Subject to any disclaimer, the term of this patent is extended or adjusted under 35 U.S.C. 154(b) by 0 days.

(21) Appl. No.: 13/989,602

(22) PCT Filed: Nov. 11, 2011

(86) PCT No.: PCT/IN2011/000779
§ 371 (c)(1),
(2), (4) Date: May 24, 2013

(87) PCT Pub. No.: WO2012/070062
PCT Pub. Date: May 31, 2012

(65) Prior Publication Data
US 2013/0245052 A1  Sep. 19, 2013

(30) Foreign Application Priority Data
Nov. 26, 2010 (IN) ............ 3577/CHE/2010

(51) Int. Cl.
*A01N 43/54* (2006.01)
*A61K 31/505* (2006.01)

(52) U.S. Cl.
USPC .......................................... 514/275; 544/295

(58) Field of Classification Search
USPC .................. 514/275; 544/295, 331
See application file for complete search history.

(56) References Cited

U.S. PATENT DOCUMENTS

| | | | |
|---|---|---|---|
| 4,216,318 A * | 8/1980 | Brown et al. | 544/310 |
| 5,436,233 A * | 7/1995 | Lee et al. | 514/63 |
| 7,169,791 B2 | 1/2007 | Breitenstein et al. | |
| 8,227,477 B2 * | 7/2012 | Sterimbaum et al. | 514/275 |
| 2006/0173182 A1 * | 8/2006 | Kankan et al. | 544/295 |
| 2010/0016590 A1 * | 1/2010 | Wang et al. | 544/297 |
| 2010/0190812 A1 | 7/2010 | Sterimbaum et al. | |

FOREIGN PATENT DOCUMENTS

| | | | |
|---|---|---|---|
| WO | WO 03000682 A1 * | 12/2003 | |
| WO | WO 2004005281 A1 * | 1/2004 | |
| WO | 2007015870 A2 | 2/2007 | |
| WO | 2007015871 A1 | 2/2007 | |
| WO | WO 2007015870 A2 * | 2/2007 | |
| WO | WO 2007015871 A1 * | 2/2007 | |
| WO | 2010009402 A2 | 1/2010 | |
| WO | WO 2010009402 A2 * | 1/2010 | |
| WO | 2010054056 A2 | 5/2010 | |
| WO | WO 2011086541 A1 * | 7/2011 | |
| WO | WO 2011163222 A1 * | 12/2011 | |
| WO | WO 2012055351 A1 * | 3/2012 | |
| WO | WO 2012070062 A2 * | 5/2012 | |

OTHER PUBLICATIONS

S.L. Morissette et al., Advanced Drug Delivery Reviews, 56, 275-300 (2004).*

(Continued)

*Primary Examiner* — James O Wilson
*Assistant Examiner* — Alexander R Pagano
(74) *Attorney, Agent, or Firm* — Cantor Colburn LLP

(57) ABSTRACT

The present invention provides a novel crystalline form of nilotinib hydrochloride, process for its preparation and pharmaceutical compositions comprising it.

14 Claims, 1 Drawing Sheet

(56) References Cited

OTHER PUBLICATIONS

S.R. Vippagunta et al., Advanced Drug Delivery Reviews, 48, 3-26 (2001).*

J.K. Guillory, Generation of Polymorphs, Hydrates, Solvates, and Amorphous Solids, in Polymorphism in Pharmaceutical Solids 183-220 (H.G. Brittain ed., 1999).*

H.G. Brittain, Preparation and Identification of Polymorphs and Solvatomorphs in, Preformulation in Solid Dosage Form Development, 185-228 (5th ed., M. C. Adeyeye et al., eds., 2008) ("Brittain").*

IP.com Number: IPCOM000183524D (May 26, 2009).*
IP.com Number: IPCOM000187328D (Sep. 2, 2009).*
IP.com Number: IPCOM000189553D (Nov. 12, 2009).*
IP.com Number: IPCOM000190565D (Dec. 6, 2009).*
IP.com number: IPCOM000197295D (Jul. 1, 2010).*

International Search Report and Written Opinion for International Application No. PCT/IN2011/00779, International Application Filing Date: Nov. 11, 2011; Date of Mailing: May 25, 2012; 5 pages.

* cited by examiner

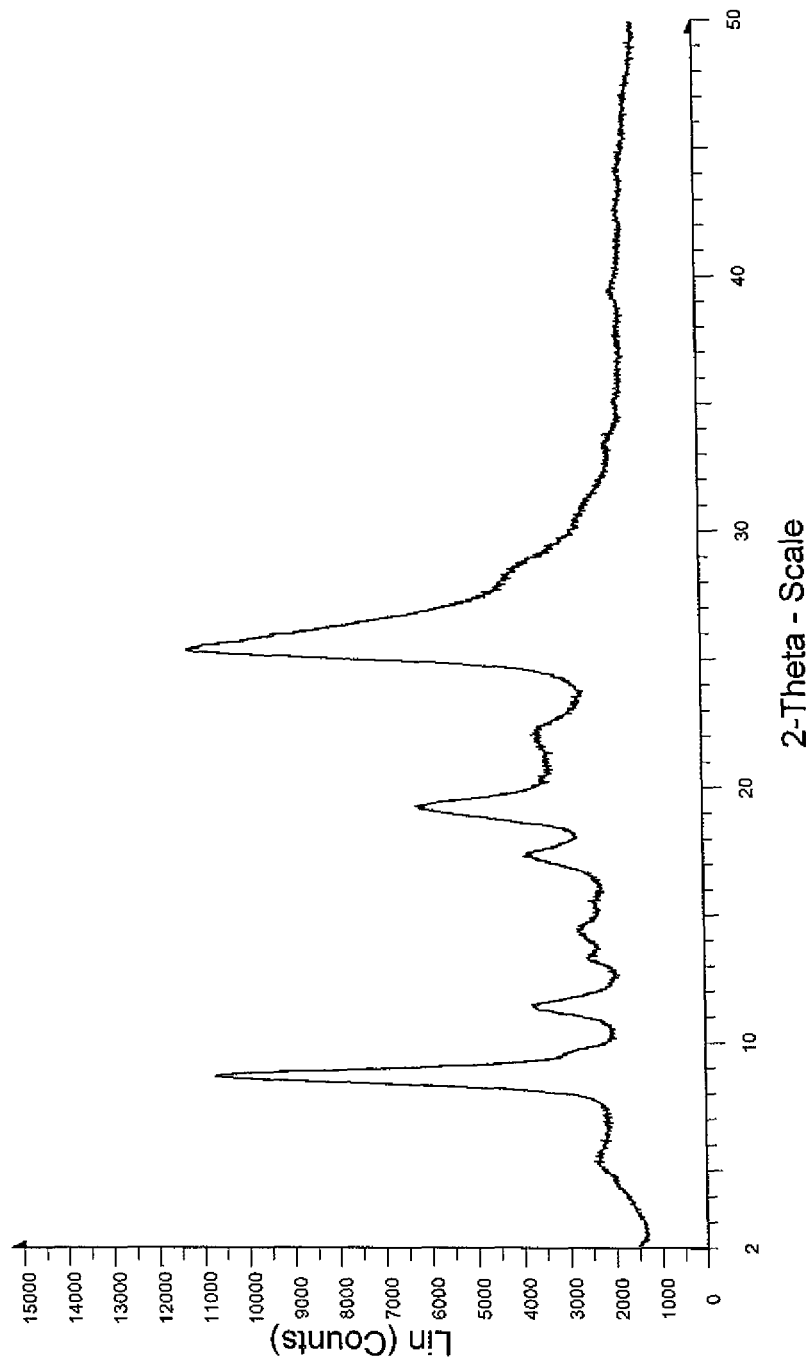

POLYMORPH OF NILOTINIB HYDROCHLORIDE

CROSS-REFERENCE TO RELATED APPLICATIONS

This is a U.S. national stage of international application No. PCT/IN2011/000779, filed on 11 Nov. 2011, the disclosure of which is incorporated herein by reference in its entirety. Priority under 35 U.S.C. §119(a) and 35 U.S.C. §365(b) is claimed from IN Patent Application No. 3577/CHE/2010, filed 26 Nov. 2010, the disclosure of which is also incorporated herein by reference in its entirety.

FIELD OF THE INVENTION

The present invention provides a novel crystalline form of nilotinib hydrochloride, process for its preparation and pharmaceutical compositions comprising it.

BACKGROUND OF THE INVENTION

Nilotinib is chemically, 4-methyl-N-[3-(4-methyl-1H-imidazol-1-yl)-5-(trifluoromethyl)phenyl]-3-[[4-(3-pyridinyl)-2-pyrimidinyl]amino]-benzamide and has the structural formula:

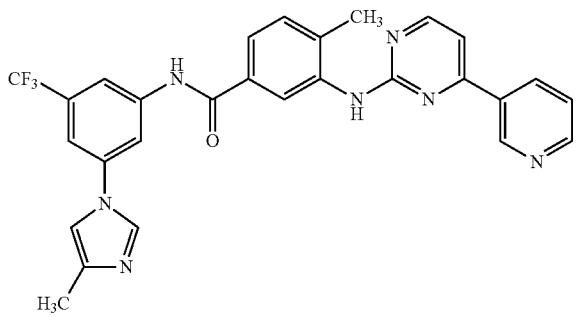 [SMILES: Cc1cn(-c2cc(NC(=O)c3ccc(C)c(Nc4nccc(-c5cccnc5)n4)c3)cc(C(F)(F)F)c2)cn1]

Nilotinib is a tyrosine kinase inhibitor used for the treatment of drug-resistant chronic myelogenous leukemia (CML), and in particular, for the treatment of chronic phase and accelerated phase Philadelphia chromosome positive chronic myeloid leukemia (CML) in adult patients whose disease has progressed on or who cannot tolerate other therapies that included imatinib. Nilotinib is administrated as a hydrochloride salt in forms of capsules that are marketed in the USA and the EU under the name Tasigna®.

Polymorphism is defined as "the ability of a substance to exist as two or more crystalline phases that have different arrangement and/or conformations of the molecules in the crystal Lattice. Thus, in the strict sense, polymorphs are different crystalline forms of the same pure substance in which the molecules have different arrangements and/or different configurations of the molecules". Different polymorphs may differ in their physical properties such as melting point, solubility, X-ray diffraction patterns, etc. Although those differences disappear once the compound is dissolved, they can appreciably influence pharmaceutically relevant properties of the solid form, such as handling properties, dissolution rate and stability. Such properties can significantly influence the processing, shelf life, and commercial acceptance of a polymorph. It is therefore important to investigate all solid forms of a drug, including all polymorphic forms, and to determine the stability, dissolution and flow properties of each polymorphic form. Polymorphic forms of a compound can be distinguished in the laboratory by analytical methods such as X-ray diffraction (XRD), Differential Scanning calorimetry (DSC) and Infrared spectrometry (IR).

Solvent medium and mode of crystallization play very important role in obtaining a crystalline form over the other.

Nilotinib and its hydrochloride salt can exist in different polymorphic forms, which may differ from each other in terms of stability, physical properties, spectral data and methods of preparation.

Nilotinib hydrochloride and its salts were disclosed in U.S. Pat. No. 7,169,791.

PCT publication no. WO 2007/015870 ('870 patent) disclosed crystalline form A, form A', form A'', form B, form B', form $S_B$, form $S_{B'}$, form C, form $S_C$, form D, form $S_E$ and amorphous form of nilotinib hydrochloride.

According to the '870 patent, crystalline form A of nilotinib hydrochloride was characterized by an X-ray powder diffraction pattern having peaks expressed as 2θ at about 8.5, 11.0, 11.5, 18.8, 19.2, 20.8, 22.1 and 26.0 degrees.

PCT publication no. WO 2010/054056 ('056 patent) disclosed crystalline form T1, form T2, form T3, form T4, form T5, form T6, form T7, form T8, form T9, form T10, form T11, form T12, form T13, form T14, form T15, form T16, form T17, form T18 and form T19 of nilotinib hydrochloride.

According to the '056 patent, crystalline form T2 of nilotinib hydrochloride was characterized by an X-ray powder diffraction pattern having peaks expressed as 2θ at about 7.1, 8.7, 11.5, 14.0, 15.3, 16.6, 17.4, 19.4 and 25.5±0.2 degrees.

According to the '056 patent, crystalline form T3 of nilotinib hydrochloride was characterized by an X-ray powder diffraction pattern having peaks expressed as 2θ at about 7.0, 8.5, 11.4, 12.1, 14.2, 17.2, 19.2, 22.1, 23.2 and 25.2±0.2 degrees.

According to the '056 patent, crystalline form T11 of nilotinib hydrochloride was characterized by an X-ray powder diffraction pattern having peaks expressed as 2θ at about 7.4, 8.7, 17.4, 25.3, 26.2 and 35.1±0.2 degrees.

According to the '056 patent, crystalline form T13 of nilotinib hydrochloride was characterized by an X-ray powder diffraction pattern having peaks expressed as 2θ at about 8.2, 12.8, 15.7, 16.5, 21.7 and 23.9±0.2 degrees.

We have discovered novel crystalline form of nilotinib hydrochloride. The novel form has been found to be stable over the time and reproducible and so, suitable for pharmaceutical preparations.

Thus, an object of the present invention is to provide a novel crystalline form of nilotinib hydrochloride, process for its preparation and pharmaceutical compositions comprising it.

SUMMARY OF THE INVENTION

In one aspect, the present invention provides a crystalline form of nilotinib hydrochloride designated as form H1 characterized by peaks in the powder x-ray diffraction spectrum having 2θ angle positions at about 8.6, 11.4, 13.2, 14.3, 15.5, 17.3, 19.2 and 25.3±0.2 degrees.

In another aspect, the present invention provides a process for the preparation of nilotinib hydrochloride crystalline form H1, which comprises:
  a) suspending nilotinib in an alcoholic solvent;
  b) heating the contents obtained in step (a) at above 65° C.;
  c) adding a solution of hydrochloride in an ester solvent to the solution obtained in step (b) at above 65° C.;
  d) maintaining the solution obtained in step (c) at above 65° C.; and
  e) isolating nilotinib hydrochloride crystalline form H1.

In another aspect, the present invention provides a process for the preparation of nilotinib hydrochloride crystalline form H1, which comprises freeze drying an aqueous solution of nilotinib hydrochloride at −80 to −90 deg C. to obtain nilotinib hydrochloride crystalline form H1.

In yet another aspect, the present invention provides a pharmaceutical composition comprising crystalline form H1 of nilotinib hydrochloride and pharmaceutically acceptable excipients.

BRIEF DESCRIPTION OF THE DRAWING

FIG. 1 is an X-ray powder diffraction spectrum of nilotinib hydrochloride crystalline form H1.

X-ray powder diffraction spectrum was measured on a bruker axs D8 advance X-ray powder diffractometer having a copper-Kα radiation. Approximately 1 gm of sample was gently flattered on a sample holder and scanned from 2 to 50 degrees two-theta, at 0.02 degrees to theta per step and a step of 10.8 seconds. The sample was simply placed on the sample holder. The sample was rotated at 30 rpm at a voltage 40 KV and current 35 mA.

DETAILED DESCRIPTION OF THE INVENTION

As used herein the term "room temperature" refers to a temperature of about 25° C. to about 35° C.

According to one aspect of the present invention, there is provided a crystalline form of nilotinib hydrochloride designated as form H1 characterized by peaks in the powder x-ray diffraction spectrum having 2θ angle positions at about 8.6, 11.4, 13.2, 14.3, 15.5, 17.3, 19.2 and 25.3±0.2 degrees. The powdered x-ray diffractogram (PXRD) of nilotinib hydrochloride crystalline form H1 is shown in FIG. 1.

The nilotinib hydrochloride crystalline form H1 may be identified and differentiated from the known polymorphs by its characteristic PXRD pattern. Thus, for example, a peak at 25.3±0.2 degrees 2θ is present and a peak at 11.0±0.2 degrees 2θ is absent in the PXRD of the nilotinib hydrochloride crystalline form H1 of the present invention, but the peak at 25.3±0.2 degrees 2θ is absent and a peak at 11.0±0.2 degrees 2θ is present in the PXRD of the nilotinib hydrochloride crystalline form A disclosed in the '870 patent. Similarly, peaks at 7.1 and 26.3 degrees 2θ are absent in the PXRD of the crystalline form H1 of the present invention, but are present in the PXRD of the crystalline form T2 disclosed in the '056 patent. Similarly, peaks at 7.0, 22.1 and 23.2 degrees 2θ are absent in the PXRD of the crystalline form H1 of the present invention, but are present in the PXRD of the crystalline form T3 disclosed in the '056 patent. Similarly, peaks at peaks at 11.3 and 13.2 are present and 7.4, 26.2 and 35.1 degrees 2θ are absent in the PXRD of the crystalline form H1 of the present invention, but are peaks at peaks at 11.3 and 13.2 are absent and 7.4, 26.2 and 35.1 degrees 2θ are present in the PXRD of the crystalline form T11 disclosed in the '056 patent. Similarly, peaks at peaks at 8.6, 13.2 and 25.3 are present and 8.2, 12.8 and 23.9 degrees 2θ are absent in the PXRD of the crystalline form H1 of the present invention, but are peaks at peaks at 8.6, 13.2 and 25.3 are absent and 8.2, 12.8 and 23.9 degrees 2θ are present in the PXRD of the crystalline form T13 disclosed in the '056 patent.

According to another aspect of the present invention, there is provided a process for the preparation of nilotinib hydrochloride crystalline form H1, which comprises:
a) suspending nilotinib in an alcoholic solvent;
b) heating the contents obtained in step (a) at above 65° C.;
c) adding a solution of hydrochloride in an ester solvent to the solution obtained in step (b) at above 65° C.;
d) maintaining the solution obtained in step (c) at above 65° C.; and
e) isolating nilotinib hydrochloride crystalline form H1.

The alcoholic solvent used in step (a) may preferably be a solvent or a mixture of solvents selected from methanol, ethanol, isopropanol, 2-butanol, 2-methyl-2-butanol and n-pentanol, and more preferably the alcoholic solvents are ethanol and 2-methyl-2-butanol.

Step (b) may preferably be carried out at about 65 to 100° C. and more preferably at about 70 to 80° C.

The ester solvent used in step (c) may preferably be a solvent or mixture of solvents selected from ethyl acetate, methyl acetate, isopropyl acetate, tert-butyl methyl acetate and ethyl formate, and more preferably the ester solvent is ethyl acetate.

The addition of hydrochloride solution in step (c) may preferably be carried out at about 65 to 100° C. and more preferably at about 70 to 80° C.

The reaction in step (b) may preferably be carried out at about 65 to 100° C. and more preferably at about 70 to 80° C.

Step (d) may preferably be maintained at about 70 to 80° C.

Isolation of nilotinib hydrochloride crystalline form H1 in step (e) can be performed by conventional methods such as cooling, removal of solvents, concentrating the reaction mass, extraction with a solvent and the like.

According to another aspect of the present invention, there is provided a process for the preparation of nilotinib hydrochloride crystalline form H1, which comprises freeze drying an aqueous solution of nilotinib hydrochloride at −80 to −90 deg C. to obtain nilotinib hydrochloride crystalline form H1.

According to another aspect of the present invention, there is provided a pharmaceutical composition comprising crystalline form H1 of nilotinib hydrochloride and pharmaceutically acceptable excipients, and optionally other therapeutic ingredients. The crystalline form H1 may preferable be formulated into tablets, capsules, suspensions, dispersions, injectables and other pharmaceutical forms.

The invention will now be further described by the following examples, which are illustrative rather than limiting.

EXAMPLES

Example 1

Preparation of Nilotinib

4-Methyl-3-[[4-(3-pyridinyl)-2-pyrimidinyl]amino]benzoic acid (55 gm), 3-(4-methyl-1H-imidazol-1-yl)-5-(trifluoromethyl)-benzenamine (45 gm), diethylcyanophosphonate (63 ml), triethylamine (78 ml) and N,N-dimethylformamide (1100 ml) were added at room temperature. The contents were heated to 60° C. and maintained for 13 hours at 60° C. The reaction mass was then cooled to room temperature and quenched with sodium bicarbonate solution (8%) and ethyl acetate. Then the layers were separated and ethyl acetate layer washed with sodium chloride solution. The separated ethyl acetate layer was then concentrated to obtain a residual solid. To the residual solid was added water (500 ml) and stirred for 30 minutes at room temperature. The separated solid was filtered and dried to obtain a solid. To the solid was added to teterahydrofuran (900 ml) and stirred for 30 minutes at 50 to 55° C. The teterahydrofuran solvent was distilled off under vacuum to obtain a residual solid. To the residual solid was added ethyl acetate (900 ml) and stirred for 1 hour at room temperature. The solid obtained was collected by filtration and dried to obtain 54 gm of nilotinib.

Example 2

Preparation of Nilotinib Hydrochloride Crystalline Form H1

Nilotinib (3 gm) as obtained in example 1 was suspended in ethanol (120 ml) and then heated to reflux. A solution of hydrochloric acid in ethyl acetate (4 ml) was added to the solution at reflux and stirred for 1 hour at reflux. The ethanol solvent was distilled off under vacuum to obtain a residual mass. To the residual mass was added ethyl acetate (50 ml) and then cooled to room temperature. The reaction mass was stirred for 1 hour at room temperature and filtered. The solid obtained was dried to give 3 gm of nilotinib hydrochloride crystalline form H1.

Example 3

Preparation of Nilotinib Hydrochloride Crystalline Form H1

Nilotinib (3 gm) was suspended in 2-methyl-2-butanol (120 ml) and then heated to 70° C. A solution of hydrochloric acid in ethyl acetate (4 ml) was added to the solution at 70° C. The solution was stirred for 30 minutes at 70° C. and then cooled to room temperature. The contents were further cooled to 10° C. and maintained for 1 hour at 10° C. The solid obtained was collected by filtration and dried to obtain 3 gm of nilotinib hydrochloride crystalline form H1.

Example 4

Preparation of Nilotinib Hydrochloride Crystalline Form H1

Nilotinib (2 gm) was added to a mixture of water (20 ml) and concentrated hydrochloric acid (0.42 ml) at room temperature to obtain a clear solution. The solution was subjected to freeze drying at about −80 deg C. for 8 hours to obtain 2 gm of nilotinib hydrochloride crystalline form H1.

We claim:

1. A nilotinib hydrochloride crystalline form H1, characterized by an x-ray powder diffractogram as shown in FIG. 1.

2. A process for the preparation of nilotinib hydrochloride crystalline form H1 as claimed in claim 1, which comprises:
   a. suspending nilotinib in an alcoholic solvent;
   b. heating the contents obtained in step (a) at above 65° C.;
   c. adding a solution of hydrochloride in an ester solvent to the solution obtained in step (b) at above 65° C.;
   d. maintaining the solution obtained in step (c) at above 65° C.; and
   e. isolating nilotinib hydrochloride crystalline form H1.

3. The process as claimed in claim 2, wherein the alcoholic solvent used in step (a) is a solvent or a mixture of solvents selected from methanol, ethanol, isopropanol, 2-butanol, 2-methyl-2-butanol and n-pentanol.

4. The process as claimed in claim 3, wherein the alcoholic solvents are ethanol and 2-methyl-2-butanol.

5. The process according to claim 2, wherein the contents are heated in step (b) at about 65 to 100° C.

6. The process according to claim 5, wherein the contents are heated at about 70 to 80° C.

7. The process as claimed in claim 2, wherein the ester solvent used in step (c) is a solvent or mixture of solvents selected from ethyl acetate, methyl acetate, isopropyl acetate, tert-butyl methyl acetate and ethyl formate.

8. The process as claimed in claim 7, wherein the ester solvent is ethyl acetate.

9. The process as claimed in claim 2, wherein the addition of hydrochloride solution in step (c) is carried out at about 65 to 100° C.

10. The process as claimed in claim 9, wherein the addition is carried out at about 70 to 80° C.

11. The process according to claim 2, wherein the solution is maintained in step (d) at about 70 to 80° C.

12. A process for the preparation of nilotinib hydrochloride crystalline form H1, which comprises freeze drying an aqueous solution of nilotinib hydrochloride at −80° C. to −90° C. to obtain nilotinib hydrochloride crystalline form H1 as claimed in claim 1.

13. A pharmaceutical composition that comprises crystalline form H1 of nilotinib hydrochloride as claimed in claim 1 and pharmaceutically acceptable excipients, and optionally other therapeutic ingredients.

14. The pharmaceutical composition as claimed in claim 13, wherein the polymorphic form is formulated into tablets, capsules, suspensions, dispersions, injectables and other pharmaceutical forms.

* * * * *